United States Patent [19]

Rasor et al.

[11] Patent Number: 5,141,738
[45] Date of Patent: Aug. 25, 1992

[54] ULTRASONIC CONTRAST MEDIUM COMPRISING GAS BUBBLES AND SOLID LIPOPHILIC SURFACTANT-CONTAINING MICROPARTICLES AND USE THEREOF

[75] Inventors: Ned S. Rasor, Cupertino, Calif.; Jurgen Hilmann, Berlin, Fed. Rep. of Germany; Lothar Lange, Berlin, Fed. Rep. of Germany; Thomas Fritzsch, Berlin, Fed. Rep. of Germany; Joachim Siegert, Berlin, Fed. Rep. of Germany; Ingfried Zimmermann, Weiler, Fed. Rep. of Germany

[73] Assignee: Schering Aktiengesellschaft, Berlin and Bergkamen, Fed. Rep. of Germany

[21] Appl. No.: 670,419

[22] Filed: Mar. 18, 1991

Related U.S. Application Data

[63] Continuation-in-part of Ser. No. 370,140, Jun. 20, 1989, abandoned, and a continuation-in-part of Ser. No. 333,408, Apr. 5, 1989, abandoned, and a continuation-in-part of Ser. No. 917,574, Oct. 10, 1986, abandoned, and a continuation-in-part of Ser. No. 600,691, Apr. 16, 1984, abandoned.

[30] Foreign Application Priority Data

Apr. 15, 1983 [DE] Fed. Rep. of Germany ....... 3313946
Apr. 15, 1983 [DE] Fed. Rep. of Germany ....... 3313947
Oct. 7, 1988 [DE] Fed. Rep. of Germany ....... 3834705

[51] Int. Cl.$^5$ .................. G01N 1/00; G01N 31/00; G01N 33/48
[52] U.S. Cl. .................. 424/2; 424/417; 424/420; 424/450
[58] Field of Search ............ 436/829; 424/2, 417, 424/420, 450

[56] References Cited

U.S. PATENT DOCUMENTS

| | | | |
|---|---|---|---|
| 4,265,251 | 5/1981 | Tickner | 128/660 |
| 4,277,367 | 7/1981 | Madsen et al. | 252/408 |
| 4,442,843 | 4/1984 | Rasor et al. | 128/660 |
| 4,466,442 | 8/1984 | Hilmann et al. | 128/653 |
| 4,572,203 | 2/1986 | Feinstein | 424/4 |
| 4,681,119 | 7/1987 | Rasor et al. | 424/9 |
| 4,684,479 | 8/1987 | D'Arrigo | 252/307 |

FOREIGN PATENT DOCUMENTS

| | | |
|---|---|---|
| 127930 | 2/1990 | China . |
| 0122624 | 10/1984 | European Pat. Off. . |
| 0123235 | 10/1984 | European Pat. Off. . |
| 3313947A1 | 10/1984 | Fed. Rep. of Germany . |
| 3637926C1 | 11/1987 | Fed. Rep. of Germany . |

OTHER PUBLICATIONS

Bommer et al., Abstract No. 770, Circulation 64(4) Oct. 1981.
Fox et al., J. Acoustical Soc. Am., 26(6) 984 (1954).
Johnson et al., Science 213, 209 (Jul. 1981).
Meltzer et al., Med. & Biol. 6, 263–269 (1980).
Roslandt et al., Contrast Echocard. Clin. App. 186 (1981).
Strasberg, M., J. Acoustical Soc. Am. 31 (2) 163 (1959).
Yount et al., Av. Space & Env. Med 48 (3) 185 (1977).
Yount, D. J. Acoust Soc. Am. 65 (6) 1429 (1979).

*Primary Examiner*—S. J. Friedman
*Attorney, Agent, or Firm*—Millen, White & Zelano

[57] ABSTRACT

Microparticles which are less than 12 μm in size and are formed of or comprise a solid lipophilic group-containing compound having an HLB value less than about 20 produce a long lived ultrasonically echogenic entity in aqueous liquid and are useful as left heart ultrasonic contrast image enhancing agents. Contrast media for ultrasonic diagnostics comprising a liquid vehicle containing (a) suspended therein microparticles of a mixture of at least one ($C_8$–$C_{20}$)-fatty acid and at least one solid that is not a surfactant and (b) microbubbles, are especially effective upon ultrasonic imaging after intravenous administration, for the contrasting of both the right heart and left heart, of the myocardium, as well as other organs, such as liver, spleen, and kidneys.

48 Claims, No Drawings

ULTRASONIC CONTRAST MEDIUM COMPRISING GAS BUBBLES AND SOLID LIPOPHILIC SURFACTANT-CONTAINING MICROPARTICLES AND USE THEREOF

CROSS REFERENCE TO RELATED APPLICATION

This application is a continuation-in-part of Ser. No. 07/370,140, now abandoned, filed Jun. 20, 1989 and of Ser. No. 07/333,408, now abandoned, filed Apr. 5, 1989, as continuation-in-parts of Ser. No. 06/917,574, now abandoned, filed Oct. 10, 1986, as a continuation-in-part of Ser. No. 06/600,691, filed Apr. 16, 1984, now abandoned, the entirety of which are incorporated by reference herein.

BACKGROUND OF THE INVENTION

This invention relates to novel ultrasonic contrast agents, their production and use, more particularly such agents which are useful as left heart contrast agents.

The ultrasonic examination of organs (sonography) is a diagnostic method that has been popular and has been practiced for a number of years. Ultrasonic waves in the megahertz range (above 2 megahertz with wavelengths of between 1 and 0.2 mm) are reflected on interfaces of various types of tissue. The thus-produced echoes are amplified and made visible. Of special significance in this connection is the examination of the heart by this method, called echocardiography. See Haft, J. I. et al.: "Clinical Echocardiography", Futura, Mount Kisco, New York 1978; Kohler, E., "Klinische Echokardiographie" [Clinical Echocardiography], Enke, Stuttgart 1979; Stefan, G., et al.: "Echokardiographie" [Echocardiography], Thieme, Stuttgart-New York 1981; G. Biamino, L. Lange: "Echokardiographie", Hoechst AG, 1983.

Since liquids, including blood, yield ultrasonic contrast only if there are differences in density with respect to the surrounding area, possibilities have been explored for making the blood and its flow visible for ultrasonic analysis, which can be achieved by the addition of extremely small gas bubbles (microbubbles).

Several methods are known in the literature for the preparation and stabilization of microbubbles. They can be produced, for example, prior to injection into the blood stream by vigorous shaking or agitation of solutions, such as saline solutions, colorant solutions, or previously drawn blood. Although ultrasonic contrast imaging has been achieved by these methods, they have serious disadvantages which manifest themselves in poor reproducibility, widely fluctuating size of the microbubbles and, due to the concurrent production of a proportion of visible, larger bubbles, the risk of embolism.

These disadvantages have been overcome, in part, by manufacturing methods such as, for example, by U.S. Pat. No. 3,640,271 wherein small bubbles of reproducible size are generated by filtration or by the use of an electrode device using direct current. Although this method has the advantage of being able to produce small gas bubbles of reproducible size, it has the disadvantage of considerable technical costs.

U.S. Pat. No. 4,276,885 describes the production of microbubbles of a definite size, which are protected from coalescence by being surrounded by a gelatin envelope. However, the finished microbubbles disclosed therein must be stored in a "frozen" condition, for example, at refrigerator temperature and prior to use they must be brought to body temperature.

U.S. Pat. No. 4,264,251 discloses the manufacture and use of gas-filled microbubbles with a solid surrounding wall of a saccharide, which bubbles can be filled with a pressurized gas. If the microbubbles are at ambient pressure, they can be utilized as ultrasonic contrast media. If they have increased internal pressure, the microbubbles can be used for blood pressure determination. Although the storage of these solid microbubbles does not present a problem, the technical expenditure in their manufacture is a considerable cost factor.

Commonly assigned U.S. Pat. No. 4,466,442 claims a method of increasing the useful lifetime and the amount of microbubbles of a size less than 50 μm produced by mechanical agitation of an aqueous liquid employed as an ultrasonic contrast medium employing a liquid containing dissolved therein a tenside which reduces the surface tension of the liquid and a compound which raises the viscosity of the liquid.

U.S. Pat. No. 4,572,203 claims a method of ultrasonic imaging for use in medical procedures which comprises injecting biodegradable, metal-containing microparticles, or microparticles comprising an amino acid matrix containing air, glass, graphite, nitrogen, carbon dioxide, metal flakes, magnetite, magnetic iron oxides or carbonyl iron, or sonicated microbubbles into an animal or human to thereby alter the acoustic properties of an area to be imaged, and then ultrasonically scanning the area so as to obtain an image.

Commonly assigned U.S. Pat. No. 4,681,119 claims a method wherein microbubbles are formed in a body liquid or carrier liquid, for example within the genitourinary or digestive systems in order to alter the transmission characteristics thereof to electromagnetic and sonic waves transmitted therethrough, by dissolving therein a solid particulate material, preferably as a suspension in a carrier liquid in which the particulate material is at least temporarily stable, the particles of which are substantially free of microbubbles and have a plurality of gas-filled voids communicating with the surface of the particles and providing nuclei for microbubble formation and the ratio of the mass of the particles to the volume of gas in the voids is sufficient to render the liquid in which the particulate material is dissolved supersaturated with respect to the gas in the voids in the area of the liquid surrounding the microbubbles when they are formed.

The following references were cited (along with DE-C-3-637 926) in the European Search Report issued in the European application corresponding to application Ser. No. 07/333,408.

EP 122 624 and EP 123 235 are European patents corresponding to the ancestor applications of application Ser. No. 07/333,408, which were combined as U.S. application Ser. No. 06/600,691, filed Apr. 16, 1984, which was abandoned in favor of continuation-in-part application Ser. No. 06/917,574, filed Oct. 10, 1986, which was abandoned in favor of application Ser. No. 07/370,140, filed Jun. 10, 1989, which will be abandoned in favor of the present application.

In parent U.S. application Ser. No. 07/333,408 (and EP 122,624), an image enhancing ultrasonic contrast agent containing microparticles and small gas bubbles is described which is suitable for enhancing, after intravenous administration and passage through the lungs, contrast imaging of the left side of the heart, of the myocardium, as well as other organs, such as the liver, the spleen, and the kidneys. The application cites fatty acids ["saturated or unsaturated ($C_4$–$C_{20}$)-fatty acids"] as being suitable for use in the production of the microparticles. Confirmation is provided by surfactant esters and salts thereof, such as, for example, ascorbyl palmitate or sucrose monopalmitate. Compared to the preferred surfactants disclosed herein, these specific surfactants are relatively quickly decomposed in the formulation even when stored under normal conditions (25° C.), which is disadvantageous for a commercial preparation and its purity requirements.

The related imaging agent of U.S. Pat. No. 4,442,843 similarly decomposes when stored.

DE-C-3-637 926, which corresponds to U.S. Pat. No. 4,684,479, cited above, describes the use of known agents, e.g., agents of EP 122 624, in an ultrasonic manometry process, which is unrelated to imaging.

The risks inherent in the use of an ultrasonic contrast medium are based in part on the size and number of any solid particles present therein as well as the size of the microbubbles therein.

Commonly assigned U.S. Pat. No. 4,442,843 (which corresponds to European Patent Application 81730118.7, Publication No. 52575), describes the production of microbubbles said to exhibit these required properties. For the manufacture of microbubbles according thereto, aggregates of particles of a solid, crystalline compound, e.g., galactose, which themselves lack microbubbles but which contain a gas which is adsorbed on the surface of the particles, occluded in cavities between the particles or is present in intracrystalline cavities, are suspended in a liquid vehicle just prior to use, thereby forming a suspension of undissolved particles and a small amount of microbubbles produced by particles dissolving in the liquid vehicle. This suspension is then injected into a blood stream within 10 minutes, where the major proportion (about 80%) of the microbubbles are formed when the undissolved aggregates in the suspension dissolve in the blood.

Although it is stated in these documents that the resultant suspension is suitable, after injection into a peripheral vein, not only for ultrasonic visualization of the right side of the heart but also, after passing through the lungs, for visualization of the left side of the heart and the blood and its flow at that location, it has not been possible to achieve reproducible and practically acceptable levels of left heart visualization employing the water soluble microbubble precursors disclosed therein. For example, when a contrast medium consisting of 400 mg. of aggregates of galactose microparticles (<8 μm; 2.5 μm mean size) in 1 ml of a 20% aqueous lactose solution was injected into a peripheral vein, it did not evoke practically significant ultrasonic echoes in the left portion of the heart, apparently because the lifetime of the microbubbles formed in the blood was too short to permit them to pass through the capillaries of the lungs. Conversely, from two specific production lots of product obtained from the same manufacturer, batches of water soluble microbubble precursor according to that patent were produced, one formed from galactose and one from maltose, which, when suspended in 1 g/ml of a 90% aqueous glucose (5% solution)/10% propylene glycol mixture and injected into a peripheral vein, evoked significant left heart contrast. However, no other lots of galactose or maltose from the same or other manufacturer did so. No explanation for this was ever found.

To ultrasonically visualize the left heart, a blood vessel flowing therefrom or an organ receiving blood therefrom, either the microbubbles or an ultrasonic contrast agent capable of producing such microbubbles in situ in the blood must be injected into a blood vessel leading from the lungs to the heart, or into an artery (a highly undesirable procedure) or the microbubbles or a microbubble precursor which produces microbubbles in situ in the blood after injection into a peripheral vein must survive the passage through the lungs. The latter alternative requires that the size of the microbubbles or the microbubble precursor be less than 12, preferably less than 8 and most preferably in the range of about 1–3 micrometers. Such small microbubbles and microbubble precursors when produced conventionally by prior art methods have an extremely short lifespan. Therefore, the chances of their surviving a passage through the lungs is highly unlikely.

EP-A-77752 discloses the preparation of a liquid mixture for use as a contrast medium consisting, in turn, of a mixture of a tenside or an aqueous solution of the tenside, and an aqueous, viscous carrier liquid.

Right heart ultrasonic contrasting for a period of time long enough for imaging thereof can readily be achieved with the water soluble microbubble precursors of U.S. Pat. No. 4,442,843 by injecting a suspension thereof in a suitable liquid carrier into a peripheral vein as a bolus, which travels essentially unmixed with blood until it reaches the right heart, where the suspension is rapidly mixed with the blood therein by hydrodynamic effects. Virtually complete loss of ultrasonic image contrast ordinarily occurs beyond the pulmonary artery. Consequently, the use of an unmodified water soluble microbubble precursor of the type disclosed in U.S. Pat. No. 4,442,843 is not feasible for left heart contrast.

U.S. Pat. No. 4,442,843 states several factors that are said to improve left heart contrast using the water soluble microbubble precursors disclosed therein. These factors may increase the very small number of microbubbles which occasionally cross the lungs during use of such materials as right heart contrast agents, but in no case does such use reproducibly result in a number of microbubbles which is of practical use for left heart contrast purposes. These factors have been found to be irrelevant for use of the improved microbubble precursors of this invention by which highly practical and reproducible left heart contrast can be achieved.

For example, U.S. Pat. No. 4,442,843 states that although for general purposes aggregates in the 30–50 micrometer size range are preferred, for traversing the lungs to image the left heart aggregates of 125 micrometer average size is preferable. However, it has since been found that these aggregates rapidly disassociate into discrete microparticles either in the presence of the liquid carrier employed therewith or in the blood, apparently as a result of the van der Waals forces, which initially caused the microparticles to coalesce into aggregates, being overcome. Therefore, increasing aggregate size does not achieve practical left heart contrasting with solid microbubble precursors of that application.

That patent also states that for left heart imaging, optimum solubility of the solid precursor is in the range of 1 mole/liter and therefore galactose is superior to the other saccharides. We have since found that notwithstanding its lower solubility compared to other saccharides, particles of galactose in the 1–3 μm range dissolve almost instantaneously in blood and therefore are no better than other saccharides for practical left heart contrasting, unless modified in accordance with this invention.

That patent also states that bubble production can be improved, inter alia, by the inclusion of a small amount of surfactant in the solid precursor or its carrier liquid. However, it has been found that conventional surfactants which have an HLB value above about 20, e.g., sodium lauryl sulfate, sodium dodecylbenzenesulfonate and the commercially available nonionic surfactants, e.g., the Pluronics, do not enhance practical left heart contrast. In fact, because such surfactants should facilitate solution of microparticles and microbubbles in blood, their use in conjunction with ultrasonic contrast agents intended for left heart imaging would appear to be contraindicated. Therefore, even with larger aggregate and smaller particle size and the use of a surfactant in the particles or in the liquid carrier, the water soluble microbubble precursors of U.S. Pat. No. 4,442,843 are not suitable for left heart ultrasonic imaging.

For the foregoing reasons, satisfactory left heart visualization with the prior art ultrasonic contrast agents, including the microbubble precursors disclosed in U.S. Pat. No. 4,442,843 could not be achieved in a predictable and reproducible manner.

The state of the prior art thus far permits the manufacture of ultrasonic contrast agents which exhibit only some of the following required or desired properties:
(1) elimination of the risk of embolism
    small gas bubbles (size and number),
    solid particles (size and number);
(2) reproducibility;
(3) adequately long stability;
(4) ability to pass through the lungs, for example, to obtain ultrasonic contrasting of the left portion of the heart and organs receiving blood therefrom;
(5) ability to pass through capillaries;
(6) sterility and freedom from pyrogens;
(7) easily produced with feasible financial expenditures; and
(8) storability without problems or special conditions.

It is an object of the present invention to provide a contrast agent suitable for altering the transmission characteristics of an aqueous liquid to an electromagnetic or elastic wave transmitted therethrough.

It is a further object of the present invention to provide a contrast agent for ultrasonic diagnostics which is capable, after intravenous administration, of ultrasonic imaging of the blood and its flow conditions not only in the right side of the heart but also, after passing through the capillary bed of the lung, in the left side of the heart and, consequently, in other organs, such as the myocardium, the liver, the spleen and the kidneys.

It is another object to provide ultrasonic contrasting methods employing these contrast agents. Other objects will be apparent to those skilled in the art to which this invention pertains.

SUMMARY OF THE INVENTION

In one composition aspect, this invention relates to solid physiologically acceptable microparticles adapted for use when mixed with an injectable aqueous liquid as an ultrasonic diagnostic agent, comprising (a) an admixture of (i) at least one $C_8$–$C_{20}$-fatty acid and (ii) at least one non-surfactant physiologically acceptable water soluble solid and (b) an amount of a gas effective to produce a suspension of microbubbles when the microparticles are dispersed in water.

In another composition aspect, this invention relates to a contrast medium adapted for use as an ultrasonic image enhancing agent comprising a liquid vehicle containing suspended therein (a) microparticles comprising a mixture of (i) at least one essentially lipophilic surfactant and (ii) at least one non-surfactant water soluble solid and (b) an amount of microbubbles effective to render the contrast medium ultrasonic image enhancing.

In another composition aspect, this invention relates to a solid sterile composition of matter suitable for use when suspended in a non-toxic physiologically acceptable intravenously injectable aqueous liquid carrier, as left heart ultrasonic contrast agent by injection of said suspension into a peripheral vein of a living being, which comprises a solid particulate microbubble precursor which is non-toxic and physiologically acceptable in an amount which, when injected, is ultrasonic image enhancing and which forms when dispersed in said liquid carrier an echogenic entity including an ultrasonically echogenic gas phase which alters the ultrasonic transmission characteristics of water or other aqueous liquid in which the echogenic entity is dispersed, wherein said microbubble precursor is or is in intimate association with an amount of a solid lipophilic group-containing compound effective to prevent the dissolution of said echogenic entity for at least about three seconds after said precursor is dispersed in said liquid carrier, said compound having an HLB (Hydrophilic-Lipophilic Balance) value, in the form that compound exists in said liquid vehicle, no greater than about 20.

In yet another composition aspect, this invention relates to a sterile injectible liquid composition of matter suitable for use as a left heart ultrasonic contrast agent which is a suspension in a non-toxic physiologically acceptable intravenously injectible aqueous liquid carrier of a solid particulate microbubble precursor of this invention.

In an article of manufacture aspect, this invention relates to kits suitable for producing the ultrasonic contrast agents of this invention.

In a process aspect, this invention relates to a method for the production of the ultrasonic contrast agents of this invention.

In a method of use aspect, this invention relates to a method for altering the transmission characteristics of an aqueous liquid to an electromagnetic or elastic wave transmitted therethrough by dispersing in said liquid an amount, effective to substantially alter said transmission characteristics, of a solid particulate microbubble precursor which forms when dispersed in said liquid an ultrasonically echogenic entity including a gas phase which alters said transmission characteristics, wherein said precursor is or is in intimate association with an amount of a solid lipophilic group-containing compound effective to prevent the dissolution of said echogenic entity for at least about three seconds after said precursor is dispersed in said liquid, said compound having an HLB (Hydrophilic-Lipophilic Balance) value, in the form that compound exists in said liquid vehicle, no greater than about 20.

In preferred method of use aspects, the aqueous liquid is the blood stream of a living being, preferably a mammal, more preferably a primate and most preferably a human being; the solid particulate microbubble precursor consists essentially of microparticles of less than 12 μm in size which are non-toxic and physiologically acceptable in the amount administered; and/or the precursor is injected into the blood stream as a suspension in a non-toxic physiologically acceptable intravenously injectable liquid carrier.

In an especially preferred method of use aspect, the suspension is injected into a peripheral vein of a living being and the pulmonary vein, the left heart or an organ receiving blood therefrom is then ultrasonically imaged.

DETAILED DISCUSSION

The contrast medium of this invention is a liquid suspension of microparticles of this invention in a liquid medium and preferably is adapted for use as an ultrasonic image enhancing agent and thus can be used as an ultasonic diagnostic agent.

Microparticles

The microparticles generally comprise from 0.01-5 wt. % (preferably 0.04-1 wt.%) of an essentially lipophilic, i.e., a lipophilic-group containing, surfactant, e.g., palmitic acid or other ($C_8$-$C_{20}$) fatty acid, and 95-99.99 wt. % (preferably 99-99.96 wt. %) of a water soluble non-surfactant, compound, e.g., galactose or other solid saccharide.

Liquid vehicle

Depending on the end use contemplated for the contrast medium, the liquid vehicle can, e.g., be water or a physiologically acceptable aqueous solution, e.g., a 0.1-30 wt. % aqueous galactose solution. In the contrast media this dissolved galactose is optionally additional to the galactose when is optionally included in the microparticles.

Contrast Medium (liquid suspension)

The contrast medium is a liquid vehicle containing about 5-50 wt. % (preferably 9-40 wt. %) of a non-surfactant, preferably water soluble compound, e.g., galactose. This concentration is nearly identical to the amount of the microparticles in the liquid suspension because the microparticles contain 95-99.99 wt. % of the non-surfactant compound.

It has been found, surprisingly, that by employing as a microbubble precursor solid microparticles as defined herein, improved ultrasonic imaging can be achieved therewith. Moreover, the period of time during which aqueous liquids are opacified with such microbubble precursors is extended substantially compared to prior art ultrasonic contrast agents.

For example, by employing such microparticles, i.e., less than 12, e.g., less than about 10, preferably less than 8 micrometers and most preferably substantially entirely about 1-3 micrometers in size, an ultrasonic contrast agent can be produced which, when injected into a peripheral vein, provides reproducible ultrasonic imaging even of blood in the arterial left-hand portion of the heart. Since it is possible to reach the left side of the heart by means of the ultrasonic contrast medium of this invention upon intravenous administration, ultrasonic contrasting of other organs supplied with blood from the aorta, such as the myocardium, the liver, the spleen, the kidneys, and others, can also be achieved after venous administration of the contrast agent.

In one aspect, the microparticles of the microbubble precursors of this invention are characterized by being or comprising an essentially lipophilic solid compound, viz., one having, in the form it exists in the aqueous liquid to be ultrasonically contrasted, an Hydrophilic-Lipophilic Balance (HLB) value no greater than about 20, preferably about 1 to 12 and most preferably about 3 to 9. See Griffin, W. C., J. Soc. Cosmetic Chemists 1, 311 (1949); ibid 5,249 (1954). Although compounds with HLB values as low as 1 can be employed, those having an HLB value of at least about 3, are preferred.

The ultrasonic contrast agents of this invention provide an entity which performs two functions, viz., the entity provides an ultrasonically echogenic gas phase and also provides a gas transport agent which enables transport of an ultrasonically echogenic gas phase through the lung capillaries. The former function is the same as that performed by the microparticles of U.S. Pat. No. 4,442,843. The latter function is not performed to an acceptable extent by the water soluble microparticles disclosed in that patent.

To act as a gas transport agent, either the solid microparticles must resist dissolution in the aqueous liquid which is to be ultrasonically imaged or the microparticles must create an environment which prolongs the life of the echogenic entity created by them in the aqueous liquid. Some of the highly hydrophobic microbubble precursors of this invention obviously possess the former property. On the other hand, it appears that all of them possess the latter property.

There are several explanations for the ability of the hydrophobized microparticles of this invention to achieve left heart contrast. Without being bound to any of them, one is that the microparticles themselves survive passage through the lung capillaries. This is theoretically possible because the microparticles are small enough to be able to do so and the gas phase produced therefrom has a lifetime long enough to produce ultrasonic contrast after their formation, e.g., at least 3 seconds and preferably 30 seconds or longer after venous injection. Another explanation is that the hydrophobizing compound prolongs the life of the microbubbles by preventing their dissolution in the blood, so that the microbubbles survive passage through the right heart and lung capillaries. This also is theoretically possible because microbubbles are known under certain circumstances to have lifetimes which far exceed their theoretical life expectancy. See Johnson, B. D. and Cooke, Robert C., Science 213,209 (1981); Yount, David E., J. Acoust. Soc. Am. 65(6) 1429 (1979); Yount, D. E., et al., Aviation, Space, and Environmental Medicine 48(3) 185 (1977), (who attributes extended microbubble lives to a "skin" of a surface active compound, i.e., one having affinity for both polar and non-polar solvents); Strasberg, M., the Journal of the Acoustical Soc. of America, 31(2) 163 (1959); and Fox, F. E. and Herefeld, K. F., ibid, 26(6) 984 (1954), who attribute the stability of small gas bubbles to an organic skin.

Irrespective of the mechanism responsible for their ability to do so, it is surprising that an ultrasonic agent upon venous injection is capable of opacifying not only the right heart but also the left heart and organs receiving blood from the latter.

Since the preferred use of the microparticles of this invention is as left heart ultrasonic contrast agents, they preferably are formed of compounds which are non-toxic and physiologically acceptable in the amounts employed. However, when an in vitro use is contemplated, their surface can be formed from or coated with other essentially lipophilic materials, e.g., water insoluble metal oxides, colloidal silica, bentonite, non-reactive methyl and phenyl silicone oils, e.g., dimethyl diethoxy silane, and reactive siloxanes, e.g., polymethylhydrogensiloxane, polyalkylenes, polytetrafluoroethylene, paraffins, natural and synthetic resins, e.g., waxes and elastomers can be used. Some of these materials are either too toxic or otherwise not physiologically acceptable, e.g., not assimilable, to be used to form the microparticles themselves when in vivo use thereof is contemplated but can nevertheless been used to render essentially hydrophobic the gas phase-containing echogenic entity created by the microparticles.

The microparticles of this invention are solids. Therefore, if they are formed solely of an essentially lipophilic compound, it must be a solid at room temperature, and preferably has a melting point above 35° C. and more preferably above 37° C. The solid must also be capable of intimately associating with or producing the requisite amount of gas. We have found that such solids generally are crystalline or brittle amorphous compounds which can be reduced by milling or precipitation to microparticle size. Preferably, the microparticles contain from about 0.02 to 0.8 ml/g of a gas in intimate association therewith. Although the microparticles preferably contain the gas which form the microbubbles in intimate association therewith, e.g., as a result of milling larger particles of the solid into microparticles, they also can be free of or substantially free of microbubbles, provided the microparticles generate an acceptable concentration of microbubbles in the aqueous liquid to be examined ultrasonically after the contrast agent is injected therein.

Because most especially lipophilic materials do not possess this physical ability to be intimately associated with 0.02 to 0.8 ml/g of a gas, and also for physiological reasons, the microparticles of this invention preferably are an intimate mixture of a water soluble non-surfactant compound, i.e., one which does not significantly affect the surface tension of water and which has the aforesaid ability to be ultimately associated with a gas and a solid lipophilic surfactant compound.

Although the preferred microparticles of this invention, like those of U.S. Pat. No. 4,442,843, are substantially free of detectable microbubbles, i.e., tiny balls or spheres of gas encapsulated by a solid membrane, and instead are intimately associated with a gas which is adsorbed on the surface of the particles or are an integral part of the internal structures of the particles, microparticles which comprise microbubbles, e.g., comparable to those of U.S. Pat. No. 4,265,251, can also be employed.

The preferred solid lipophilic group-containing compounds suitable for producing the microparticles of this invention are those that are physiologically acceptable in the amounts utilized, i.e., they are non-toxic and are biodegradable or otherwise assimilable in the body in such amounts.

Examples of suitable solid lipophilic group containing compounds are lecithins, lecithin fractions and their modification products, polyoxyethylene fatty acid esters, such as polyoxyethylene fatty alcohol esters, polyoxyethylated sorbitan fatty acid esters, glycerol polyethylene glycol oxystearate, glycerol polyethylene glycol ricinoleate, ethoxylated soy sterols, ethoxylated caster oils and the hydrogenated derivatives thereof, cholesterol solid, fatty acids, preferably $C_8$-$C_{20}$, e.g., stearic acid, myristic acid, palmitic acid, arachic acid, polyoxyethylene fatty acids, esters, e.g., such as sugar esters, for example, sucrose esters, e.g., sucrose dipalmitate and sucrose monolaurate, or sucrose glycerides, as well as xyloglycerides, saturated and unsaturated, preferably $C_8$-$C_{20}$-, fatty alcohols, fatty acids or fatty acid esters, mono-, di-, and triglycerides, sorbitan fatty acids and physiologically acceptable salts thereof, polyoxyethylene fatty acid esters, fatty acid esters of sucrose or fatty acid esters, such as butyl stearate and ascorbyl palmitate, xyloglycerides, such as soybean oil sucrose glyceride, and palm oil xylitol, palm oil sucrose glyceride, cottonseed oil sucrose glyceride.

Preferred are myristic, palmitic, stearic and arachic acid and a mixture thereof, most preferably palmitic acid.

In addition to the free acids, the salts thereof can also be employed, provided they have the requisite HLB value no greater than 20. Examples of such salts are metal salts, e.g., sodium, potassium, calcium, magnesium salts, ammonium salts and salts of organic bases, e.g., of a primary, secondary or tertiary amine, e.g., ethanolamine diethanolamine, triethanolamine, glucamine, N-methylglucamine and N,N-dimethylglucamine salts.

If the contrast agent is to be injected into a blood stream, the salt should be physiologically acceptable. Preferred salts are sodium, calcium and magnesium stearate, ascorbyl palmitate and the sucrose esters of lauric acid, of stearic acid and of palmitic acid.

The solid water soluble, i.e., to the extent of at least about 0.5 mol. per liter, non-surfactant compounds which are employed in the contrast agents of this invention include both organic and inorganic compounds, e g., inorganic salts, such as sodium chloride and potassium chloride, organic salts, such as sodium citrate, sodium acetate and sodium tartrate, and solid hydroxy, preferably polyhydroxy compounds, such as saccharides, e.g., monosaccharides, such as glucose, fructose and galactose, disaccharides such as sucrose, lactose and maltose, pentoses, such as arabinose, xylose and ribose, trisaccharides and cyclic and polysaccharides, e.g., cyclodextrins, such as $\alpha$, $\beta$, or $\tau$-cyclodextrin, and polyols. Preferred are galactose, fructose, glucose, lactose and $\alpha$-cyclodextrin.

The essentially lipophilic surfactant compound is preferably present in the microparticles of the ultrasonic contrast agents of this invention in amounts corresponding to a concentration thereof about 0.01–5% by weight, preferably 0.04–1% by weight. The water soluble non-surfactant compound, when present, is employed in the liquid suspensions in amounts corresponding to a concentration therein of about 5–50% by weight, preferably about 9–40% by weight.

The water soluble component is present in the microparticles of the ultrasonic contrast agents of this invention in a weight ratio therein to the lipophilic group-containing compound is from about 10,000:1 to 20:1, preferably about 2500:1 to about 100:1, e.g., the water soluble component is present in the microparticles at a concentration of 95–99.99 wt. %, preferably 99–99.96 wt. % and the microparticles contain about 0.01–5 wt. %, preferably about 0.04–1 wt. % thereof of the essentially lipophilic compound.

The gas-containing microparticles employed in this invention can be produced by grinding the solid or solids employed in the contrast agent in an air jet mill, until the desired particle size has been objected and the requisite gas absorption has been achieved. A particle size range of <1 to 50 μm is usually produced. Preferably, at least 99% of the particles are less than 12 μm, preferably less than 10 μm, and most preferably less than 8 μm in size, with median size preferably being about 1-3 μm. The microparticles can also comprise a small proportion, e.g., up to about 1% by weight, of larger particles, e.g., up to 50 μm in size. These larger particles cannot pass through the lung but will contribute to the contrasting of the right heart. The particle size can be determined with conventional measuring devices in the usual manner.

These microparticles usually coalesce when produced into aggregates which are held together by van der Waals forces. When the microparticles are mixed with the liquid carrier or, at the very latest, where the microparticles are injected into the blood stream, these aggregates rapidly disassociate into discrete microparticles.

When a mixture of a lipophilic group-containing surface active compound and water soluble compound is employed, they can be coprecipitated from solution or preferably the water soluble compound is first recrystallized or reprecipitated under sterile conditions and the lipophilic group-containing compound is then intimately mixed therewith and the mixture comminuted to the desired particle size. The solid surface active compound can also be mixed with the water soluble compound as a solution in available organic solvent, which is then removed from the mixture prior to the commutation step, e.g., with heating and preferably under a vacuum.

As stated above, the volume of gas which is intimately associated with the microparticles usually is in the range of about 0.02-0.8 ml per gram of microparticles.

Because of their small size, either the microparticles obtained by the comminuting process, or the microbubbles produced therefrom, or both, can pass harmlessly through the lung and other capillary systems, thereby precluding the formation of embolisms.

As stated above, the gas required for ultrasonic contrasting is transported to the desired site as the gas phase of the entity produced when the microparticles are dispersed in the aqueous liquid, either in intimate association with undissolved microparticles or as gas released from gas absorbed on the surface of the microparticles, occluded in the cavities between the microparticles or in an intercrystalline fashion in the microparticles themselves when the microparticles dissolve, or gas precipitated from solution by salting out, or a combination of the above.

The storage stability of the microparticles, i.e., their ability to retain the gas associated therewith upon storage, is partially dependent on the temperature and the selected essentially lipophilic compound present therein as can be seen from the table below.

TABLE 1

STABILITY STUDY

Formulation: A Galactose + 0.134% Ascorbyl Palmitate
B Galactose + 0.1% Palmitic Acid Chemical Stability of Additives in Dependence on Storage Temperature and Time (% of original gas retained)

| Storage Period | FORMULATION | |
|---|---|---|
| | A | B |
| | % (m/m) | % (m/m) |
| Start | 100% | 100% |
| 6 weeks | | |
| Room Temperature | 84.3% | Not analyzed |
| 40° C. | 67.9% | Not analyzed |

TABLE 1-continued

STABILITY STUDY

Formulation: A Galactose + 0.134% Ascorbyl Palmitate
B Galactose + 0.1% Palmitic Acid Chemical Stability of Additives in Dependence on Storage Temperature and Time (% of original gas retained)

| Storage Period | FORMULATION | |
|---|---|---|
| | A | B |
| | % (m/m) | % (m/m) |
| Start | 100% | 100% |
| 50° C. 12 weeks | 33.6% | 97.4% |
| Room Temperature | 79.8% | 98.0% |
| 40° C. | 53.7% | 98.4% |
| 50° C. | 18.7% | 95.1% |

A reduction in surfactant content is also accompanied by a decrease in left-heart contrast.

The liquid vehicle of the contrast agents of this invention, besides performing the function of rendering the microparticles injectable and transportable in the blood, stabilizes the suspension of microparticles and any microbubbles formed therein prior to injection, for example, by preventing sedimentation of the microparticles, coalescing of the gas bubbles and/or delaying the dissolution of the microparticles in the blood.

Suitable liquid carriers are water, aqueous solutions of one or more inorganic salts, such as physiologically acceptable saline and buffer solutions, aqueous solutions of mono- or di-saccharides, such as galactose, glucose and lactose, mono- or polyhydric galactose, glucose and lactose, mono- or polyhydric alcohols, e.g., ethanol, propanol, isopropyl alcohol, polyethylene glycol, ethylene glycol, glycerol, propylene glycol, propylene glycol methyl ether, or aqueous solutions thereof, at concentrations at which as they are physiologically acceptable and injectable.

Preferred liquid carriers are water and aqueous physiological electrolyte solutions, such as physiological saline solutions, and aqueous solutions of a water soluble, essentially non-surfactant solution, as described above, e.g., galactose and glucose. When solutions are employed, the concentration of the dissolved compound can range from about 0.1% by weight to saturation, e.g., up to 30% by weight, preferably 0.5-25% by weight. Water, aqueous sodium chloride, preferably physiological, e.g., 0.9%, solutions, and aqueous galactose, e.g., up to 20%, preferably 5-6%, solutions are preferred. Preferably, the liquid carrier has a surface tension greater than about 55 dynes/cm.

The weight ratio of liquid vehicle to microparticles, in the ultrasonic contrast agent as initially formed, is usually about 1:1 to 10:1 and preferably about 2:1 to 4:1 weight ratio. In general, about 1-500, preferably 10-400 mg of microparticles are used per ml. of suspension. In some instances, some but not all of the microparticles dissolve in the liquid carrier and form microbubbles therein before the suspension is injected in the blood.

A preferred embodiment of the microparticles is a mixture of particles of a particle size of less than 10 μm of a mixture of about 99.9% galactose and about 0.1% palmetic acid. In a preferred embodiment of the contrast agent, these particles are suspended at about a 1:2 to 1:4 ratio in sterile water.

In a process aspect, this invention also relates to a process for the preparation of an ultrasonic contrast agent of this invention.

To produce a ready-for-use ultrasonic contrast agent of this invention, the sterile liquid vehicle is mixed aseptically with the above-described microparticles and this mixture is gently agitated, e.g., by stirring, shaking or inverting the mixture several times, until a homogeneous suspension is produced. The resultant suspension is then injected into the blood stream, preferably as soon as possible after its preparation and within about 5 minutes thereafter, as a bolus directly into a peripheral vein or into a catheter previously inserted therein, in a volume of about 0.01 ml to 1 ml per kg of body weight and in a total dose of about 1 to 50 ml, preferably about 3 to 8 ml.

For practical reasons, since the final contrast agent may have a useful life of no more than about 5 minutes after its production, the carrier liquid and the microparticles are stored separately, preferably under sterile conditions and more preferably in sealed containers containing the amounts required for a single examination and having seals which permit aseptic withdrawal of the carrier liquid from its container and injection into the container containing the microparticles with an injection syringe. A conventional glass vial with a top which can be snapped off is a suitable container for the carrier liquid. A conventional rubber stoppered glass vial can be used for the microparticles and also for the carrier liquid as well. The internal volume of the container for the microbubbles must be such that the contents of the carrier liquid container can be transferred thereto and the mixture agitated to produce the requisite suspension.

In a product aspect this relates to a kit for producing a contrast agent of this invention comprising two such containers, viz., a) a first sealed container having an internal volume of about 5-10 ml, provided with a seal permitting aseptic addition of a liquid thereto and withdrawal of a liquid therefrom and containing from about 1 to 5 g, e.g., 2 or 3 g, of sterile microparticles, as defined herein above; and b) a second sealed container, provided with a seal permitting aseptically withdrawal of the contents thereof, and containing a liquid vehicle for the microparticles, e.g., about 2 to 10 ml, e.g., preferably 4 to 8.5 ml of a sterile physiologically acceptable injectable liquid.

In a preferred method of use aspect of this invention, a sterile suspension of the microparticles and microbubbles generated therefrom in the sterile liquid vehicle is injected as a bolus in the vein of a living being, preferably a mammal, more preferably a primate and most preferably a human being, thereby introducing an echogenic entity into the blood stream thereof, and thereafter the left heart, a blood vessel flowing therefrom or an organ receiving blood therefrom is ultrasonically visualizing in a conventional manner.

In one aspect of the in vivo method-of-use aspect of this invention, all of the microparticles are converted into microbubbles in the carrier liquid before injection of the latter into the blood stream. To achieve such a total conversion requires that the microparticles consist predominantly of a compound which is readily soluble in the selected carrier liquid, that the lipophilic group-containing compound in intimate association therewith permits access of the liquid carrier to the soluble compound and that the microbubbles thus formed have a significant life span, e.g., at least two and preferably 5-20 seconds or more life span after injection into the blood stream. Those combinations of soluble compound, lipophilic group-containing compound and liquid carrier which are operable in such a method can readily be determined by routine experimentation.

The use of the contrast medium according to this invention can be demonstrated by performing an echocardiographic examination on a baboon weighing 10 kg:

8.5 ml of liquid vehicle (see preparation examples) is withdrawn with an injection syringe from a vial and added to 3 g of microparticles present in a second vial, and shaken for about 5-10 seconds until a homogeneous suspension has been formed. Of this suspension, 2 ml is injected into a peripheral vein (V. jugularis, brachialis or saphena) by way of a three-way valve at an infusion rate of at least 1 ml/sec, preferably 2-3 ml/sec. The injection of 10 ml of physiological sodium chloride solution immediately follows the injection of contrast medium at the same rate, so that the contrast medium bolus remains intact as long as possible. Before, during, and after injection, a commercially available transducer for echocardiography is held against the thorax of the test animal so that a typical cross section is obtained through the right and left heart. This testing arrangement corresponds to the state of the art and is known to those skilled in the art.

Once the ultrasonic contrast medium has reached the right heart, an observation can be made in the 2-D echo image or in the M-mode echo image of how the blood labeled by the contrast medium first reaches the level of the right atrium, then the level of the right ventricle and the pulmonary artery, homogeneous filling prevailing for a time period adequate for diagnostic examination. While the cavities of the right heart become empty again the ultrasonic image, the blood labeled with contrast medium reappears, after passing through the lungs, in the pulmonary veins, fills the left atrium, the left ventricle, and the aorta in a homogeneous fashion, the contrast remaining longer than on the right side of the heart. In addition to imaging of the blood flow through the cavities of the left heart, a contrast image of the myocardium is likewise obtained, reflecting blood circulation.

The use of the ultrasonic contrast medium of this invention is, however, not limited to rendering the bloodstream visible in the arterial portion of the heart after venous administration; rather, with excellent success, the contrast medium is also employed in the examination of the right heart and other organs by contrast medium.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application West German P 38 34 705.9 filed Oct. 7, 1988, are hereby incorporated by reference.

EXAMPLES

Preparations—Liquid Vehicles

(A) 20% Galactose Solution

Prepared by dissolving 80 g of galactose in water suitable for injection to a volume of 400 ml, filtering the solution through a 0.2 μm filter, and dispensing 4 ml portions of the filtrate into 5 ml vials, which are then sealed and sterilized for 20 minutes at 120° C.

(B) Water 4 ml portions of water suitable for injection purposes are filled into 5 ml vials, which are then sealed and sterilized for 20 minutes at 120° C.

(C) Physiological Saline

Prepared by dissolving 4.5 g of sodium chloride in water to a volume of 500 ml, filtering the solution through a 0.2 μm filter, and dispensing 4 ml portions of the solution.

(D) 10% lactose solution

Produced by dissolving 50 g of lactose in water suitable for injection purposes to a volume of 500 ml, filtering the solution through a 0.2 μm filter and dispensing 4 ml portions thereof into 5 ml vials, which are then sealed and sterilized for 20 minutes at 120° C.

EXAMPLE 1

Microparticles

Under sterile conditions, 198 g of galactose are thoroughly blended with 2 g of magnesium stearate by homeopathic trituration, the mixture passed through a 0.8 mm screen, loosely mixed and then ground with an air jet mill until the following distribution of particle size has been achieved:

| Median | 1.9 μm |
|---|---|
| 99% | <6 μm |
| 90% | <3 μm |

Determination of the particle size and its distribution is accomplished in a particle measuring device after suspension of an aliquot of the particles in anhydrous isopropanol. The microparticles are dispensed aseptically in 2 g portions into 5 ml sterile vials which are then sealed.

Contrast Agent

To produce 5 ml of a ready-for-use ultrasonic contrast agent, the contents of one vial of liquid vehicle (A) is withdrawn therefrom with an injection syringe and then injected into a vial containing microparticles of this example and the mixture agitated until a homogeneous suspension is produced (5-10 seconds).

EXAMPLE 2

Microparticles

Under sterile conditions, 198 g of galactose are thoroughly mixed with 2 g of ascorbyl palmitate by homeopathic trituration and the mixture is then further processed as described in Example 1, resulting in the following particle size distribution:

| Median | 1.9 μm |
|---|---|
| 100% | <6 μm |
| 90% | <3 μm |

Determination of the particle size is effected as described in Example 1. 1,200 mg portions of the microparticles are dispensed into sterile 5 ml vials, which are then sealed.

Contrast Agent

To prepare 4.5 ml of a ready-for-use ultrasonic contrast agent, the contents of one vial of liquid vehicle (B) is withdrawn therefrom with an injection syringe and then injected into a vial containing microparticles of this example and the mixture agitated until a homogeneous suspension is obtained (5-10 seconds).

EXAMPLE 3

Microparticles

Under sterile conditions, 198 g of lactose (anhydrous, particle size 0.3 mm) is thoroughly mixed with 2 g of ascorbyl palmitate by homeopathic trituration and the mixture is then further processed as described in Example 1, resulting in the following particle size distribution:

| Median | 1.9 μm |
|---|---|
| 100% | <6 μm |
| 90% | <3 μm |

Determination of the particle size is effected as described in Example 1. 1,200 mg portions of the microparticles are dispensed into sterile 5 ml vials, which are then sealed.

Contrast Agent

To prepare 4.5 ml of a ready-for-use ultrasonic contrast agent, the contents of one vial of liquid vehicle (C) is withdrawn therefrom with an injection syringe and then injected into a vial containing microparticles of this example and the mixture agitated until a homogeneous suspension is obtained (5-10 secs.).

EXAMPLE 4

Microparticles

Under sterile conditions, 199 g of α-cyclodextrin are thoroughly blended with 1 g of ascorbyl palmitate by homeopathic trituration and the mixture is then processed further as described in Example 1, thus obtaining microparticles having the following particle size distribution:

| Median | 2 μm |
|---|---|
| 99% | <6 μm |
| 90% | <4 μm |

Determination of the particle size is effected as described in Example 1. 400 mg portions of the microparticles are filled into 5 ml vials, which are then sealed.

Contrast Agent

To prepare 4 ml of a ready-for-use ultrasonic contrast agent, the content of one vial of saline solution (C) is withdrawn therefrom with an injection syringe and then injected into a vial containing microparticles of this example and the mixture agitated until a homogeneous suspension is obtained (5-10 secs.).

EXAMPLE 5

Microparticles

Under sterile conditions ascorbyl palmitate is dissolved in methanol, the solution filtered through a 0.2 μm filter, recrystallized under sterile conditions, dried, and passed through a 0.8 mm screen. The sterile ascorbyl palmitate is then ground in an air jet mill under sterile conditions until the following particle size distribution is attained:

| Median value | 1.9 μm |
|---|---|
| 99% | <6 μm |
| 90% | <3 μm |

Determination of the particle size and its distribution is performed in a particle measuring device after suspension of an aliquot of the particles in cold aqueous 0.1% strength "Pluronic" F68 solution.

The microparticles are dispensed aseptically in 40 mg portions into sterile 5 ml vials, which are then sealed.

Contrast Agent

To prepare 4 ml of a ready-for-use ultrasonic contrast agent, the contents of one vial with liquid vehicle (D) is withdrawn therefrom with an injection syringe and then injected into a vial containing microparticles of this example and the mixture agitated until a homogeneous suspension is obtained.

EXAMPLE 6

Microparticles

Under sterile conditions, a sterile-filtered solution of 0.5 g of ascorbyl palmitate in 40 g of isopropanol is applied to 199.5 g of sterile galactose particles, the isopropanol is evaporated from the resulting mixture by drying at 40° C. and under 200 torr vacuum and the resulting product is comminuted in an air jet mill until the following particle size distribution has been attained:

| Median value | 1.9 μm |
|---|---|
| 99% | <6 μm |
| 90% | <3 μm |

Determination of particle size and its distribution is accomplished in a particle measuring device, for example after suspension of an aliquot of the particles in isopropanol. The microparticles are dispensed aseptically 2 g portions into 5 ml vials which are then sealed.

Contrast Agent

To prepare 5 ml of a ready-for use ultrasonic contrast agent, the contents of one vial of liquid carrier (C) is withdrawn therefrom with an injection syringe and then injected into a vial containing microparticles of this example and the mixture agitated until a homogeneous suspension is obtained (5-10 seconds).

EXAMPLE 7

Microparticles

Under sterile conditions, 199.5 g of galactose are triturated with 0.5 g of ascorbyl palmitate, thoroughly mixed, the mixture passed through a 0.8 mm screen, and then comminuted in an air jet mill until the following particle size distribution is achieved:

| Median value | 1.9 μm |
|---|---|
| 99% | <6 μm |
| 90% | <3 μm |

Determination of particle size and its distribution is carried out in a particle size measuring instrument, for example after suspension of an aliquot of the particles in isopropanol. 2 g portions of the microparticles are packaged in 5 ml vials, as described in Example 1.

Contrast Agent

To prepare 5 ml of a ready-for use ultrasonic contrast medium, the contents of one vial of liquid vehicle (C) is withdrawn with an injection syringe and then injected into the vial with microparticles of this example and agitated until a homogeneous suspension has been produced (5-10 seconds).

EXAMPLE 8

Microparticles

Under sterile conditions 0.5 g of sucrose monopalmitate is triturated with 199.5 g of galactose, thoroughly blended and the mixture passed through a 0.8 mm screen and then ground with an air jet mill until the following particle size distribution is reached:

| Median value | 1.9 μm |
|---|---|
| min. 99% | <6 μm |
| min. 90% | <3 μm |

Determination of particle size and its distribution is made in a particle measuring device, for example after suspension of an aliquot of the particles in isopropanol. The microparticles are packaged in 2 g portions in 5 ml vials as described above.

Contrast Agent

To prepare 5 ml of a ready-for-use ultrasonic contrast agent, the contents of one vial of liquid vehicle (B) is withdrawn with an injection syringe and injected into a vial of microparticles of this example and the mixture agitated until a homogeneous suspension is formed (5-10 seconds).

EXAMPLE 9

Microparticles

Under sterile conditions, a sterile-filtered solution of 0.5 g of sucrose monopalmitate in 40 g of isopropanol is applied to 199.5 g of sterile galactose particles, the isopropanol is evaporated from the mixture by drying at 40° C. and under 200 torr, and the product is ground with an air jet mill until the following particle size distribution is obtained:

| Median value | 1.9 μm |
|---|---|
| min. 99% | <6 μm |
| min. 90% | <3 μm |

Determination of particle size and its distribution is effected in a particle measuring device for example after suspension of an aliquot in isopropanol. 2 g portions of the microparticles are packaged in 5 ml vials as described above.

Contrast Agent

To prepare 5 ml of a ready-for-use ultrasonic contrast agent, the contents of one vial of liquid vehicle (B) is withdrawn with an injection syringe and then injected into a vial of microparticles of this example and the mixture agitated until a homogeneous suspension is produced (5–10 seconds).

EXAMPLE 10

A. Microparticles

Under sterile conditions, a sterile-filtered solution of 0.5 g of sucrose monostearate in 40 g of isopropanol is applied to 199.5 g of sterile galactose particles, the isopropanol is evaporated from the mixture at 400° C. and 200 torr, and the product is ground in an air jet mill until the following particle size distribution is obtained:

| Median value | 1.9 μm |
|---|---|
| min. 99% | <6 μm |
| min. 90% | <3 μm |

Determination of particle size and its distribution is effected in a particle measuring instrument, for example after suspension of an aliquot in isopropanol. The microparticles are packaged in 2 g portions in 5 ml vials as described above.

Contrast Agent

To prepare 5 ml of a ready-for use ultrasonic contrast agent, the contents of one vial of liquid vehicle (B) is withdrawn with an injection syringe and injected into a vial of microparticles of this example and the mixture agitated until a homogeneous suspension is formed (5–10 seconds).

B. Microparticles

Under sterile conditions, 0.5 g of sucrose monostearate is triturated with 199.5 g of galactose, mixed thoroughly, the mixture passed through a 0.8 mm screen and then ground with an air jet mill until the following particle size distribution is obtained:

| Median value | 1.9 μm |
|---|---|
| min. 99% | <6 μm |
| min. 90% | <3 μm |

The particle size and its distribution are determined in a particle measuring device, for example after suspension of an aliquot in isopropanol. 2 g portions of the microparticles are packaged in 5 ml vials as described above.

Contrast Agent

To prepare 5 ml of a ready-for-use ultrasonic contrast agent, the contents of one vial of liquid carrier (B) is withdrawn with an injection syringe and then injected into a vial of microparticles of this example and the mixture agitated until a homogeneous suspension is produced (5–10 seconds).

EXAMPLE 11

Microparticles

Under sterile conditions, a sterile-filtered solution of 0.5 g of sucrose distearate is applied in 40 g of isopropanol to 199.5 g of sterile galactose particles, the isopropanol is removed from the mixture by drying at 40° C. and under 200 torr, and the product is ground with an air jet mill until the following particle size distribution is obtained:

| Median value | 1.9 μm |
|---|---|
| min. 99% | <6 μm |
| min. 90% | <3 μm |

Determination of particle size and its distribution is effected in a particle measuring device, for example after suspension of an aliquot isopropanol. 2 g portions of the mioroparticles are packaged in 5 ml vials as described above.

Contrast Agent

To prepare 5 ml of a ready-for-use ultrasonic contrast medium, the contents of one vial of liquid vehicle (B) is withdrawn with an injection syringe and injected into a vial of microparticles of this example and the mixture agitated until a homogeneous suspension is formed (5–10 seconds).

EXAMPLE 12

Microparticles

Under sterile conditions, 0.5 g of sucrose distearate is triturated with 199.5 g of galactose, thoroughly blended and the mixture passed through a 0.8 mm screen and then ground with an air jet mill until the following particle size distribution is obtained:

| Median value | 1.9 μm |
|---|---|
| min. 99% | <6 μm |
| min. 90% | <3 μm |

Determination of particle size and its distribution takes place in a particle measuring instrument, for example after suspension of an aliquot in isopropanol. 2 g portions of the microparticles are packaged in 5 ml vials as described above.

Contrast Agent

To prepare 5 ml of a ready-for-use ultrasonic contrast medium, the content of one vial of liquid vehicle (B) is withdrawn with an injection syringe and injected in a vial of microparticles of this example and the mixture agitated until a homogeneous suspension is obtained (5–10 seconds).

EXAMPLE 13

Microparticles (A) Dissolve 0.4 g of a solid film forming lipophilic group-containing compound, e.g., stearic acid or sodium stearate, in a non-aqueous, volatile solvent, e.g., ethanol (160 ml.), with heating (to about 40° C.). Mix 100 g. of a saccharide microbubble precursor as disclosed in U.S. Pat. No. 4,442,843 (whose disclosure is incorporated herein by reference), e.g., galactose, and heat below the boiling point of the solvent for about 15 minutes to ensure thorough wetting of the saccharide with the solvent. Pour off any supernatant liquid and dry the saccharide particles in a vacuum. Reduce the saccharide particles to the desired size by grinding and sieving through a 100 μm sieve or preferably with an air jet mill, e.g., to min. 99% <6 μm.

(B) Dissolve 0.126 g of stearic acid and 250 g of commercially available galactose in 275 ml water and heat until a clear solution is obtained. Filter through a 0.45 μm filter and rapidly cool, refrigerate the precipitated solids under vacuum for 12 hours. Turn the solids, and dry for an additional 24 hours. Pulverize and sieve or grind them in an air jet mill to the desired microparticle size, e.g., min. 99% <6 μm.

Contrast Agent

Form a uniform suspension of 1 g of microparticles (A) or (B) of this example in 2 ml. of sterile aqueous dextrose (5%) or 10% propylene glycol/90% aqueous dextrose (5%) by stirring or agitation.

Inject 1 g of 2 g of the microparticles in the suspension within 5 minutes of preparation into the peripheral vein of an anesthetized dog and ultrasonically examine the left heart of the dog. About 5 seconds after injection, left heart contrast is achieved and persists for up to about 20 seconds.

EXAMPLE 14

Microparticles

Solution 1

1.183 g of palmitic acid and 0.90 g of D(−)-N-methylglucamine are dissolved in 60 g of ethanol and filtered aseptically through a 0.2 μm filter with a sterile container to provide a sterile ethanolic solution thereof.

Solution 2

1000 g of galactose is dissolved in 538 g of purified water, sterile filtered over a 0.2 μm filter and cooled to about 15° C. Solution 1 is added to solution 2 aseptically and the solvent mixture is drawn off at 40° C. and 50 m bar. The dry recrystallizate is micronized aseptically with an air jet mill, the size distribution of the particles should exhibit the following characteristic values:

| Median value | 1.8–2.0 μm |
|---|---|
| 90% | <6 μm |
| 99% | <8 μm |

Particle size and distribution is determined in a particle size measuring device, e.g., the granulometer 715 after suspension in isopropanol. The microparticles (2 g each) are transferred aseptically into 10 conventional rubber stoppered ml vials.

Contrast Agent

The 4 ml contents of a vial of liquid vehicle (B) (sterile for injection purposes) is transferred aseptically by injection spraying into a vial of the thus-produced microparticles and shaken for 5–10 seconds until a homogeneous suspension is produced, thereby producing a ready for use ultrasonic contrast agent.

EXAMPLE 5

Microparticles

Solution 1

1000 g of galactose is dissolved in 53B g of purified water, filtered aseptically through a 0.2 μm filter into a sterile container and cooled to about 15° C. to provide a sterile ethanolic galactose solution.

Solution 2

2 g of ascorbyl palmitate are dissolved in 60 g of ethanol and filtered aseptically through an 0.2 μm filter into a sterile container to provide a sterile ethanolic solution of ascorbyl palmitate.

Solutions 1 and 2 are combined and the solvent mixture is drawn off aseptically at 40° C. and 50 m bar. The dry recrystallizate is comminuted aseptically with an air jet mill until the following size distribution of the particles is achieved:

| Median value | 1.8–2.0 μm |
|---|---|
| 90% | <6 μm |
| 99% | <8 μm |

Particle size distribution is determined in a particle size measuring device, e.g., a granulometer 715 after suspension in isopropanol. Packaging of the microparticles (2 g each) are transferred into conventional rubber stoppered 10 ml-vials.

Contrast Agent

The 4 ml contents of a vial of liquid vehicle (B) (sterile injection purposes) is transferred aseptically by injection spraying into a vial of the thus-produced microparticles and shaken until a homogeneous suspension is produced (5–10 seconds), thereby producing a ready-to-use ultrasonic contrast agent.

EXAMPLE 16

Use of Ultrasonic Contrast Agent

The use of the contrast agent of this invention is demonstrated by conducting an echocardiographic examination of a baboon weighing 10 kg.

5 ml of liquid vehicle (A) is removed aseptically from a vial thereof with a sterile injection syringe and injected into a vial containing 2 g of the microparticles of Example 1. The mixture is agitated for about 5–10 seconds until a homogeneous suspension has been formed and 2 ml of this suspension is immediately withdrawn from the vial with a sterile injection syringe and injected into a peripheral vein (V. jugularis, brachialis, or saphena) of the baboon by way of a catheter therein through a three-way valve, at the rate of at least 1 ml/sec, preferably 2-3 ml/sec. The injection of contrast agent is immediately followed by the injection at the same rate of 10 ml of physiological saline solution, so that the bolus of contrast medium remains intact as much as possible until the right portion of the heart has been reached. Before, during and after injection, a commercially available sonar transducer for echocardiography is held against the thorax of the test animal so that a typical cross section is obtained through the right and left heart. This testing arrangement corresponds to the state of the art and is well known to those skilled in the art.

Once the ultrasonic contrast medium has reached the right heart, an observation can be made in the 2-D echo image or in the M mode echo image of how the blood labeled by the contrast agent first reaches the level of the right atrium, then the level of the right ventricle and the pulmonary artery, with homogeneous filling of the heart prevailing for about 10 seconds. While the cavities of the right heart become empty again in the ultrasonic image, the blood labeled by contrast agent reappears, after passing through the lungs, in the pulmonary veins, fills the left atrium, the left ventricle and the aorta in a homogeneous fashion, with the ultrasonic contrast persisting two to three times longer than on the right side of the heart. Besides an imaging of the blood flow through the cavities of the left heart, the myocardium is likewise made visible, reflecting the blood flow through it.

The use of the ultrasonic contrast agent of this invention is not limited to rendering the bloodstream visible in the arterial portion of the heart after venous administration. The contrast agent is also employed with excellent success in the ultrasonic examination of the right heart and other organs.

EXAMPLE 17

(A) Liquid Vehicle: Water for purposes of injection (B) Preparation of Microparticles I. 1,998 g of galactose in 1,080 g of water is purified, dissolved, filtered under sterile conditions, and cooled under aseptic conditions to 6°–10° C.

II. 2 g of palmitic acid is dissolved in 120 g of ethanol, filtered under sterile conditions, and added to I under agitation.

III. The combined solutions are dried under aseptic conditions at about 40° C. and under a vacuum of 50 mbar.

IV. The recrystallized product is comminuted under aseptic conditions by means of an air jet mill to the following grain size distribution:

$D_{10} \leq 1$ μm
$D_{50} \leq 2.5$ μm
$D_{90} \leq 5$ μm

Determination of the grain size distribution takes place after suspending the micronized product in alcohol with the use of a particle measuring device (e.g., Cilas Granulometer 715).

V. Packaging of the microparticles is effected into 20 ml vials at respectively 3 g.

(C) Production of Ready-For-Use Ultrasonic Contrast Medium

By means of an injection syringe, 8.5 ml of water for injection purposes is transferred into the 20 ml vial containing 3 g of microparticles, and the vial is shaken until a homogeneous suspension is obtained (5–10 seconds).

EXAMPLE 18

(A) Liquid Vehicle: Water for injection purposes (B) Preparation of Microparticles I. 1,998 g of galactose in 1,080 g of water is purified, dissolved, filtered under sterile conditions, and cooled under aseptic conditions to 6°–10° C.

II. 2 g of myristic acid is dissolved in 120 g of ethanol, filtered under sterile conditions, and added to I under agitation.

III. The combined solutions are dried under aseptic conditions at about 40° C. and under a vacuum of 50 mbar.

IV. The recrystallized product is comminuted under aseptic conditions with an air jet mill to the following grain size distribution:

$D_{10} \leq 1$ μm
$D_{50} \leq 2.5$ μm
$D_{90} \leq 5$ μm

Determination of grain size distribution takes place after suspending the micronized product in alcohol with a particle measuring instrument (e.g., Cilas Granulometer 715).

V. Packing of the microparticles takes place into 20 ml vials, 3 g each.

(C) Production of Ready-For-Use Ultrasonic Contrast Medium

Using an injection syringe, 8.5 ml of water for injection purposes is transferred into the 20 ml vial containing 3 g of microparticles, and the vial is shaken until a homogeneous suspension is produced (5–10 seconds).

EXAMPLE 19

(A) Liquid Vehicle: Water for injection purposes (B) Preparation of Microparticles I. 1,998 g of galactose in 1,080 g of water is purified, dissolved, filtered in sterile state, and cooled under aseptic conditions to 6°–10° C.

II. 2 g of stearic acid is dissolved in 120 g of ethanol, filtered under sterile conditions, and added to I with stirring.

III. The combined solutions are brought to the dry condition in an aseptic environment at about 40° C. and under a vacuum of 50 mbar.

IV. The recrystallized product is comminuted under aseptic conditions by means of an air jet mill to the following grain size distribution:

$D_{10} \leq 1$ μm
$D_{50} \leq 2.5$ μm
$D_{90} \leq 5$ μm

Determination of grain size distribution is made after suspending the micronized product in alcohol using a particle measuring device (e.g., Cilas Granulometer 715).

V. The microparticles are packaged into 20 ml vials, 3 g each.

(C) Production of Ready-For-Use Ultrasonic Contrast Medium

With the use of an injection syringe, 8.5 ml of water for injection purposes is transferred into the 20 ml vial containing 3 g of microparticles, and the vial is shaken until a homogeneous suspension is obtained (5–10 seconds).

EXAMPLE 20

(A) Liquid Vehicle: Water for injection purposes (B) Preparation of Microparticles I. 1,998 g of galactose in 1,080 g of water is purified, dissolved, filtered in the sterile state, and cooled to 6°–10° C. under aseptic conditions.

II. 1 g of myristic acid + 1 g of arachic acid are dissolved in 120 g of ethanol, filtered under sterile conditions, and added to I under stirring.

III. The combined solutions are brought to dryness under aseptic conditions at about 40° C. and under a vacuum of 50 mbar.

IV. The recrystallized product is aseptically comminuted with the use of a jet air mill to the following grain size distribution:

$D_{10} \leq 1$ μm
$D_{50} \leq 2.5$ μm
$D_{90} \leq 5$ μm

Determination of the grain size distribution takes place after suspending the micronized product in alcohol using a particle measuring device (e.g., Cilas Granulometer 715).

V. The microparticles are packaged into 20 ml vials, 3 g each.

(C) Production of Ready-For-Use Ultrasonic Contrast Medium

By means of an injection syringe, 8.5 ml of water for injection purposes is transferred into the 20 ml vial containing 3 g of microparticles, and the vial is shaken until a homogeneous suspension is obtained (5-10 seconds).

EXAMPLE 21

(A) Production of Liquid Vehicle 55 g of galactose is dissolved in water for injection purposes, filled up to a volume of 1,000 ml, filtered through a 0.2 μm filter, respectively 10 ml of the filtered solution is dispensed into 10 ml vials, and sterilized for 15 minutes at 121° C.

(B) Preparation of Microparticles

I. 1,998 g of galactose in 1,080 g of water is purified, dissolved, filtered under sterile conditions, and aseptically cooled to 6°-10° C.

II. 1 g of palmitic acid +1 g of stearic acid are dissolved in 120 g of ethanol, filtered under sterile conditions, and added to I under agitation.

III. The combined solutions are aseptically dried at about 40° C. and under a vacuum of 50 mbar.

IV. The recrystallized product is comminuted under aseptic conditions with an air jet mill to the following grain size distribution:

$D_{10} \leq 1$ μm
$D_{50} \leq 2.5$ μm
$D_{90} \leq 5$ μm

Determination of the grain size distribution is effected after suspending the micronized product in alcohol, using a particle size measuring device (e.g., Cilas Granulometer 715).

V. The microparticles are packaged into 20 ml vials, 3 g each.

(C) Production of Ready-For-Use Ultrasonic Contrast Medium

Using an injection syringe, 8.5 ml of galactose solution A is transferred into the 20 ml vial which contains 3 g of microparticles, and the vial is shaken until a homogeneous suspension is obtained (5-10 seconds).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An injectable contrast medium adapted for use as an ultrasonic diagnostic agent comprising a physiologically acceptable liquid vehicle containing suspended therein
   (a) microparticles comprising a mixture of (i) an amount effective to render the contrast medium suitable for use as a left heart imaging agent of at least one physiologically acceptable, essentially lipophilic surfactant selected from the group consisting of a lecithin, a lecithin fraction, a modification product of a lecithin fraction, a polyoxyethylene fatty acid ester, a polyoxyethylated sorbitan fatty acid ester, glycerol polyethylene glycol oxystearate, glycerol polyethylene glycol ricinoleate, an ethoxylated soy sterol, an ethoxylated castor oil, a hydrogenated derivative of an ethoxylated castor oil, cholesterol, a ($C_8$–$C_{20}$)-fatty acid, a physiologically acceptable salt of a ($C_8$–$C_{20}$) fatty acid, a polyoxyethylene fatty acid, a sugar ester, a sucrose glyceride, an oxyloglyceride, a saturated ($C_4$–$C_{20}$)-fatty alcohol, an unsaturated ($C_4$–$C_{20}$) fatty alcohol, a fatty acid, a fatty acid ester, a mono-, di-, or triglyceride, a sorbitan fatty acid, a physiologically acceptable salt of a sorbitan fatty acid, a polyoxyethylene fatty acid ester, ascorbyl palmitate, a xyloglyceride, a palm oil sucrose glyceride and a cottonseed oil sucrose glyceride, and (ii) at least one non-surfactant physiologically acceptable water soluble solid selected from the group consisting of an inorganic salt, an organic salt and a solid hydroxy compound; and
   (b) an amount of microbubbles effective to render the contrast medium ultrasonic image enhancing.

2. A contrast medium of claim 1, wherein the microparticles comprise 0.01-5% by weight of the surfactant.

3. A contrast medium of claim 1, wherein the surfactant is a ($C_8$–$C_{20}$)-fatty acid.

4. A contrast medium of claim 3, wherein the fatty acid myristic, palmitic, stearic or arachic acid or a mixture thereof.

5. A contrast medium of claim 3, wherein the fatty acid is palmitic acid.

6. A contrast medium of claim 1, wherein the microparticles comprise 95-99.99% by weight of the non-surfactant water soluble solid.

7. A contrast medium of claim 1, wherein the non-surfactant water soluble solid is a saccharide.

8. A contrast medium of claim 7, wherein the saccharide is a galactose, fructose, glucose, lactose or alphacyclodextrin.

9. A contrast medium according to claim 7, wherein the saccharide is galactose.

10. A contrast medium according to claim 1, wherein the microparticles have a particular size of less than about 10 μm.

11. A contrast medium of claim 1, wherein the physiologically acceptable liquid vehicle is water, a physiological electrolyte solution, an aqueous solution of a mono- or polyhydric alcohol or of propylene glycol methyl ether, or an aqueous solution of a monosaccharide or a disaccharide.

12. A contrast medium of claim 1, wherein the liquid vehicle is water or an aqueous galactose solution.

13. A contrast medium of claim 1, wherein the physiologically acceptable liquid vehicle is water or an aqueous galactose solution and wherein the microparticles have a particle size of less than about 10 μm and comprise 99–99.96% wt. % of a saccharide and about 0.04–1 wt. % of a ($C_8$–$C_{20}$)-fatty acid.

14. A contrast medium of claim 13, wherein the microparticles are a mixture of palmitic acid and galactose.

15. A contrast medium of claim 1, wherein the microparticles have a size less than about 10 μm and consist essentially of about 99.9% by weight of galactose and about 0.1% by weight of palmitic acid and wherein the liquid vehicle is water.

16. Solid physiologically acceptable microbubble precursor particles adapted for use when mixed with an injectable aqueous liquid as an injectable ultrasonic diagnostic agent in the form of aggregates comprising (a) microparticles of an admixture of (i) an amount effective to render the contrast medium suitable for use as a left heart imaging agent of at least one physiologically acceptable, essentially lipophilic surfactant selected from the group consisting of a lecithin, a lecithin fraction, a modification product of a lecithin fraction, a polyoxyethylene fatty acid ester, a polyoxyethylated sorbitan fatty acid ester, glycerol polyethylene glycol oxystearate, glycerol polyethylene glycol ricinoleate, an ethoxylated soy sterol, an ethoxylated castor oil, a hydrogenated derivative of an ethoxylated castor oil, cholesterol, a ($C_8$–$C_{20}$)-fatty acid, a physiologically acceptable salt of a ($C_8$–$C_{20}$) fatty acid, a polyoxyethylene fatty acid, a sugar ester, a sucrose glyceride, an oxyloglyceride, a saturated ($C_4$–$C_{20}$)-fatty alcohol, an unsaturated ($C_4$–$C_{20}$) fatty alcohol, a fatty acid, a fatty acid ester, a mono-, di-, or triglyceride, a sorbitan fatty acid, a physiologically acceptable salt of a sorbitan fatty acid, a xyloglyceride, a palm oil sucrose glyceride and a cottonseed oil sucrose glyceride, and (ii) at least one non-surfactant physiologically acceptable water soluble solid selected from the group consisting of an inorganic salt, an organic salt, and a solid hydroxy compound; and (b) an amount of a gas effective to produce a suspension of microbubbles when the microbubble precursor particles are dispersed in water.

17. Solid microbubble precursor particles of claim 16, wherein the microparticles have a particle size less than about 10 μm.

18. Solid microbubble precursor particles of claim 16, wherein the surfactant is a ($C_8$–$C_{20}$)-fatty acid.

19. Solid microbubble precursor particles of claim 16, wherein the microparticles consist essentially of 95–99.99% by weight of a saccharide and 5–0.01% by weight of the fatty acid.

20. Solid microbubble precursor particles of claim 19, wherein the saccharide is galactose, fructose, glucose, lactose or alpha-cyclodextrin.

21. Solid microbubble precursor particles of claim 19, wherein the fatty acid is palmitic, myristic, stearic or arachic acid.

22. Solid microbubble precursor particles of claim 19, wherein the fatty acid is palmitic acid and wherein the saccharide is galactose.

23. Solid microbubble precursor particles of claim 19, wherein the microparticles have a size less than about 10 μm and consist essentially of about 99.9% by weight of galactose and about 0.1% by weight of palmitic acid.

24. A kit adapted for the preparation of an injectable ultrasound contrast medium, which kit comprises a first container containing solid microbubble precursor particles of claim 16, and a second container containing a physiologically acceptable injectable liquid vehicle for the precursor particles which, when mixed therewith, forms an injectable contrast medium suitable for use as a left heart imaging agent.

25. A kit according to claim 24, wherein the microparticles comprise 0.01—5% by weight of the surfactant.

26. A kit according to claim 4, wherein the surfactant is a ($C_8$–$C_{20}$)-fatty acid.

27. A kit according to claim 26, wherein the fatty acid is myristic, palmitic, stearic or arachic acid or a mixture thereof.

28. A kit according to claim 26, wherein the fatty acid is palmitic acid.

29. A kit according to claim 24, wherein the microparticles comprise 95–99.99% by weight of the non-surfactant water soluble solid.

30. A kit according to claim 24, wherein the non-surfactant water soluble solid is a saccharide.

31. A kit according to claim 30, wherein the saccharide is galactose, fructose, glucose, lactose, or alphacyclodextrin.

32. A kit according to claim 31, wherein the saccharide is galactose.

33. A kit according to claim 24, wherein the microparticles have a particular size of less than about 10 μm.

34. A kit according to claim 24, wherein the physiologically acceptable liquid vehicle is water, a physiological electrolyte solution, or an aqueous solution of a mono- or polyhydric alcohol, of propylene glycol methyl ether, or of a monosaccharide or a disaccharide.

35. A kit according to claim 24, wherein the liquid vehicle is water or an aqueous galactose solution.

36. A kit according to claim 24, wherein the physiologically acceptable liquid vehicle is water or an aqueous galactose solution and wherein the microparticles have a particle size of less than about 10 μm and comprise 99–99.96% wt. % of a saccharide and about 0.04–1 wt. % of a ($C_8$–$C_{20}$)-fatty acid.

37. A kit according to claim 36, wherein the microparticles are a mixture of palmitic acid and galactose.

38. A kit according to claim 24, wherein the microparticles have a size less than about 10 μm and consist essentially of about 99.9% by weight of galactose and about 0.1% by weight of palmitic acid and the liquid vehicle is water.

39. A method for altering the transmission characteristics of an aqueous liquid to an electromagnetic or elastic wave transmitted therethrough by dispersing in the liquid an amount effective to alter said transmission characteristics of a solid microbubble precursor particles which contains an amount of a gas effective to produce a suspension of microbubbles which alters the transmission characteristics of the liquid when the precursor is dispersed in the liquid and which, when dispersed in the liquid, forms an ultrasonically ectogenic entity including a gas phase which alters those transmission characteristics, which comprises employing a microbubble precursor containing a solid phase consisting essentially of an intimate mixture of 95–99.99% by weight of (a) at least one water soluble solid selected from the group consisting of an inorganic salt, an organic salt and a solid hydroxy compound, and (b) an amount from 5-0.01% by weight of a solid lipophilic group-containing compound effective to prevent the dissolution of the water soluble solid for at least about three seconds after the precursor is dispersed in the liquid, which lipophilic group-containing compound has an HLB (Hydrophilic-Lipophilic Balance) value, in the form that compound exists in the liquid, of no greater than about 20 and is selected from the group consisting of a lecithin, a lecithin fraction, a modification product of a lecithin fraction, a polyoxyethylene fatty acid ester, a polyoxyethylated sorbitan fatty acid ester, glycerol polyethylene glycol oxystearate, glycerol polyethylene glycol ricinoleate, an ethoxylated soy sterol, an ethoxylated castor oil, a hydrogenated derivative of an ethoxylated castor oil, cholesterol, a ($C_8$-$C_{20}$)-fatty acid, a physiologically acceptable salt of a ($C_8$-$C_{20}$) fatty acid, a polyoxyethylene fatty acid, a sugar ester, a sucrose glyceride, an oxyglyceride, a saturated ($C_4$-$C_{20}$)-fatty alcohol, an unsaturated ($C_4$-$C_{20}$) fatty alcohol, a fatty acid, a fatty acid ester, a mono-, di-, or triglyceride, a sorbitan fatty acid, a physiologically acceptable salt of a sorbitan fatty acid, a polyoxyethylene fatty acid ester, ascorbyl palmitate, a xyloglyceride, a palm oil sucrose glyceride and a cottonseed oil sucrose glyceride, which microbubble precursor also comprises (c) an amount of a gas effective to produce a suspension of microbubbles when the solid phase is dispersed in the liquid.

40. The method according to claim 39, wherein the aqueous liquid is the blood stream of a living being, the particulate solid is non-toxic and physiologically acceptable in the amount dispersed therein and is injected into the blood stream as a suspension in a non-toxic physiologically acceptable intravenously injectable liquid vehicle.

41. The method according to claim 39, wherein the surfactant is a ($C_8$-$C_{20}$)-fatty acid.

42. The method according to claim 41, wherein the fatty acid is myristic, palmitic, stearic or arachic acid or a mixture thereof.

43. The method according to claim 41, wherein the fatty acid is palmitic acid.

44. The method according to claim 39, wherein the non-surfactant water soluble solid is a saccharide.

45. The method according to claim 44, wherein the saccharide is galactose, fructose, glucose, lactose or alphacyclodextrin.

46. The method according to claim 44, wherein the saccharide is galactose.

47. The method according to claim 41, wherein the physiologically acceptable liquid vehicle is water or an aqueous galactose solution and wherein the microparticles have a particle size of less than about 10 μm and comprise 99-99.96% wt. % of a saccharide and about 0.04-1 wt. % of a ($C_8$-$C_{20}$)-fatty acid.

48. The method according to claim 47, wherein the microparticles are a mixture of palmitic acid and galactose.

* * * * *